United States Patent [19]

Tepic

[11] Patent Number: 5,052,243
[45] Date of Patent: Oct. 1, 1991

[54] HAND POWER TOOL MECHANISM

[75] Inventor: Slobodan Tepic, Davos, Switzerland

[73] Assignee: Laboratorium für experimentelle Chirurgie, Davos, Switzerland

[21] Appl. No.: 337,528
[22] PCT Filed: Aug. 15, 1987
[86] PCT No.: PCT/EP87/00450
  § 371 Date: Mar. 22, 1989
  § 102(e) Date: Mar. 22, 1989
[87] PCT Pub. No.: WO89/01322
  PCT Pub. Date: Feb. 23, 1989
[51] Int. Cl.⁵ .......................... A61F 2/46; B26B 13/26
[52] U.S. Cl. ..................... 74/523; 222/326;
  606/93; 606/92; 30/251; 81/415
[58] Field of Search ............. 30/189, 192, 238, 249,
  30/251, 252; 81/304, 305, 345, 346, 377, 415,
  378; 222/391, 473, 81, 326; 254/209, 210, 243,
  244, 245, 248; 606/92-94; 74/523

[56] References Cited

U.S. PATENT DOCUMENTS 1,238,733  9/1917  Arden ................................ 222/391
2,442,424  6/1948  McGary et al. ....................... 30/251
3,572,192  3/1971  Juras .................................. 81/415
4,368,577  1/1983  Babb .................................. 30/251

OTHER PUBLICATIONS

A. A. Amis, "Variation of Finger Forces in Maximal Isometric Grasp Tests on a Range of Cylinder Diameters", J. Biomed. Eng., 1987, vol. 9, Oct., pp. 313-320.

Primary Examiner—Stephen C. Pellegrino
Assistant Examiner—Glenn K. Dawson
Attorney, Agent, or Firm—Walter C. Farley

[57] ABSTRACT

This hand power tool mechanism is useful for caulking guns in particular. It has a stationary handle (101), a drive lever (102) connected to said stationary handle (101) by a joint (103), a movable handle (104) connected to said drive lever (102) by a joint (105) and a linkage closure bar (106) connected to both said movable handle (104) and said stationary handle (101) by joints (107) and (108) respectively. Said stationary handle (101), drive lever (102), movable handle (104), linkage closure bar (106) and said four joints (103, 105, 107, 108) are forming a four bar linkage mechanism which allows an optimum utilization of the hand power.

9 Claims, 4 Drawing Sheets

HAND POWER TOOL MECHANISM

FIELD OF THE INVENTION

This invention relates to a hand power tool mechanism having a stationary handle, and a drive lever connected to said stationary handle by a joint. More particularly the invention relates to a bone cement caulking gun.

BACKGROUND OF THE INVENTION

Bone cement is used for the anchoring of prosthetic replacements in human bones. It is prepared by mixing a powder component (mainly consisting of polymethylmethacrylate beads and a polymerization catalyst) with a liquid component (mainly consisting of methylmethacrylate monomer) and is applied to the site of implantation by a caulking gun which is used to expel the bone cement mixture in a state of relatively high viscosity. For this purpose the mixed bone cement is filled into a syringe and is extruded by a piston. The power for driving the piston is produced by the action of the hand through a drive mechanism of the friction or ratchet type. In conventional bone cement caulking guns the handles are arranged in a simple kinematic pair, i.e., a pair of pivoted, relatively movable handles in which the position of the strongest fingers is unfavorable for delivering power to the piston.

SUMMARY OF THE INVENTION

The invention is intended to remedy these drawbacks. It solves the problem of how to design a hand power tool with favorable conditions for delivering hand power to the advance mechanism of the tool, in particular a bone cement caulking gun. The invention is equally useful for other hand powered tools, like scissors, pliers or guns for delivering silicone rubber.

The advantages offered by the invention are mainly the better utilisation of hand power.

In a preferred embodiment the four joints of a four-bar linkage mechanism are arranged in such a way that an optimal force/travel ratio for the fingers of the hand results. In particular the two lines connecting the proximal with the distal joints preferably intersect at a point distally to the mechanism from the little finger, preferably at 0.5 to 2.5 lengths of the linkage closure bar.

In a further preferred embodiment of the hand power tool mechanism according to the invention the kinematic joints are replaced by flexible joints, preferably made of elastomer allowing a simpler construction and avoiding cleaning problems especially for surgical applications.

The hand power tool mechanism according to the invention can be used e.g. for a bone cement or silicone rubber caulking gun, for scissors or pliers. The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

DESCRIPTION OF THE PREFERRED EMBODIMENTS

Figure 1:
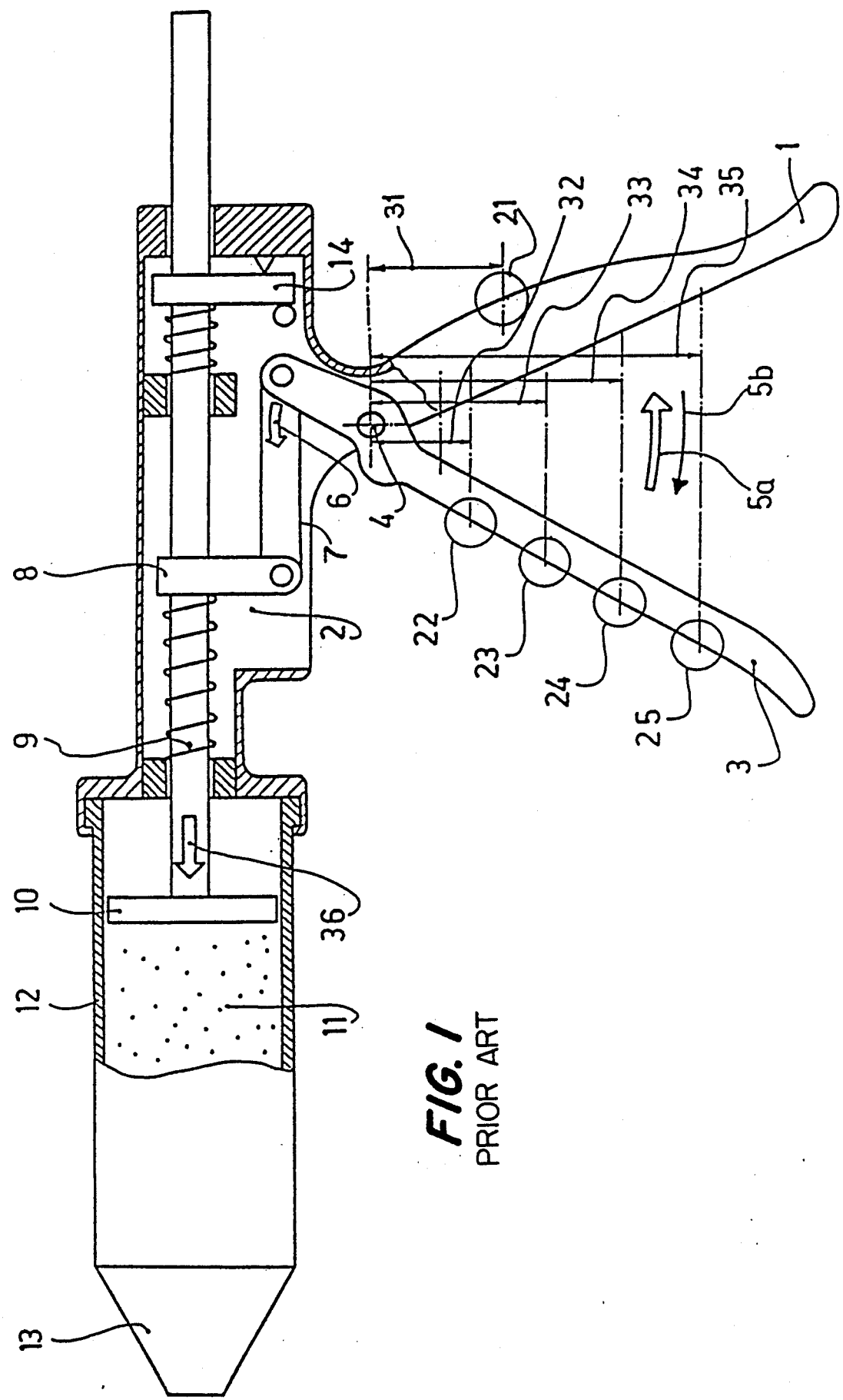
FIG. 1 is a sectional view of a conventional bone cement caulking gun.

FIG. 1 represents a conventional bone cement caulking gun with a stationary handle 1 connected to the body 2 and a movable handle 3 pivotally connected to the stationary handle 1 by means of the pivot point 4. Movement of the handle 3 as indicated by arrow 5a results in the movement indicated by arrow 6 of the bar 7 which advances rod 9 via pusher 8. Piston plate 10 advances forwardly as indicated by arrow 36 for each squeeze of the handles 1,3 extruding material 11 from the syringe 12 through a nozzle 13. On the return stroke, the direction of which is indicated by arrow 5b, the rod 9 is prevented from retracting by a brake 14. Position of the hand on the handles 1,3 is indicated by circles 21 for the palm, 22 for the index, 23 for the middle finger, 24 for the ring-finger and 25 for the little finger acting through lever arms 31,32,33,34,35 respectively, as measured from pivot point 4. The strongest fingers (index and middle finger) have the shortest lever arms 32,33. The energy transmitted to the piston plate 10 is equal to the product of the force and travel of each of the fingers. The utilisation of the strongest fingers of the hand is consequently poor.

The number of strokes per minute one can execute with the hand is obviously limited and so is the power delivered to the tool.

Figure 2:
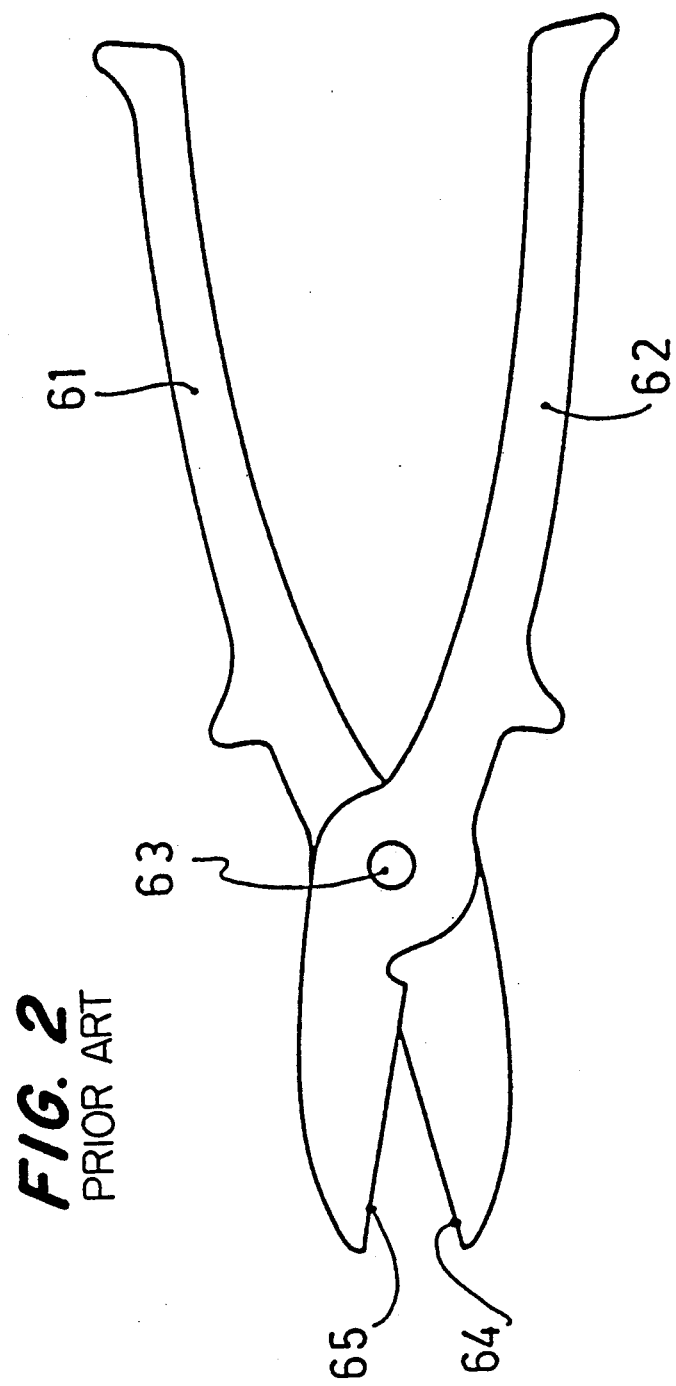
FIG. 2 is a perspective view of a conventional scissors.

FIG. 2 represents conventional scissors where two handles 61, 62 are connected at the pivot joint 63. The position of the hand is identical to that described in FIG. 1 and consequently the power delivered to the blades 64,65 does not correspond to the full potential of the hand.

Figure 3:
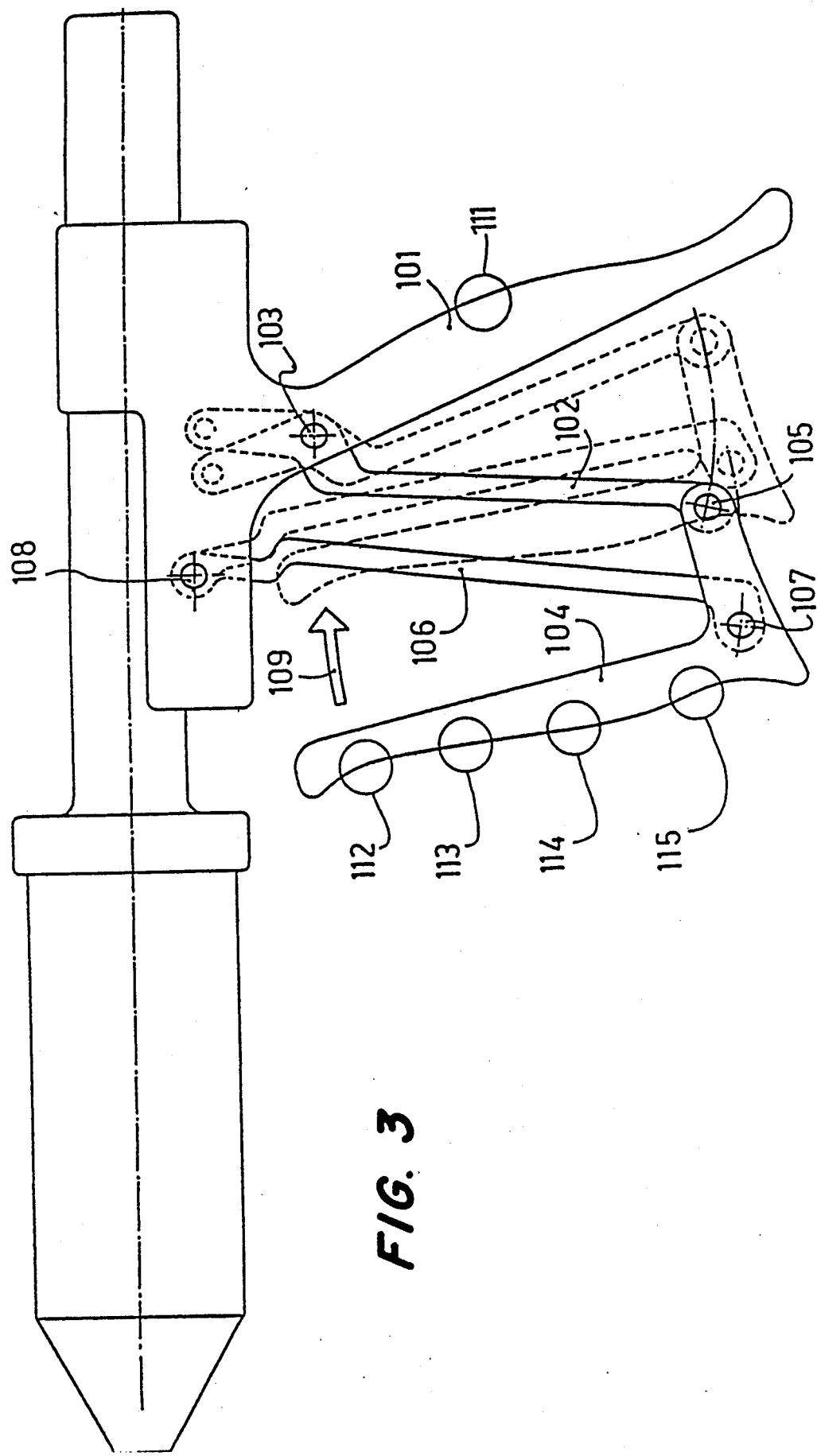
FIG. 3 is a four bar linkage caulking gun according to the invention.

FIG. 3 represents a caulking gun according to the invention. Its hand power tool mechanism comprises a stationary handle 101, a drive lever 102 connected to stationary handle 101 by a pivot joint 103, a movable hand 104 connected to drive lever 102 by a pivot joint 105 and a linkage closure bar 106 connected to both movable handle 104 and stationary handle 101 by pivot joints 107 and 108 respectively. Stationary handle 101, drive lever 102, movable handle 104, linkage closure bar 106 and the four joints 103,105,107,108 form a four-bar linkage mechanism. The movement of movable handle 104 (as shown by arrow 109) from the open position to the closed position (as represented by the dotted lines) and back is defined by the kinematics of the four bar linkage. The respective positions of the palm and fingers is indicated by the circles 111,112,113,114,115. The position of the strongest fingers (index and middle finger) is favorable for power delivery through a mechanism within the body of the gun similar to the one described in FIG. 1.

Figure 4:
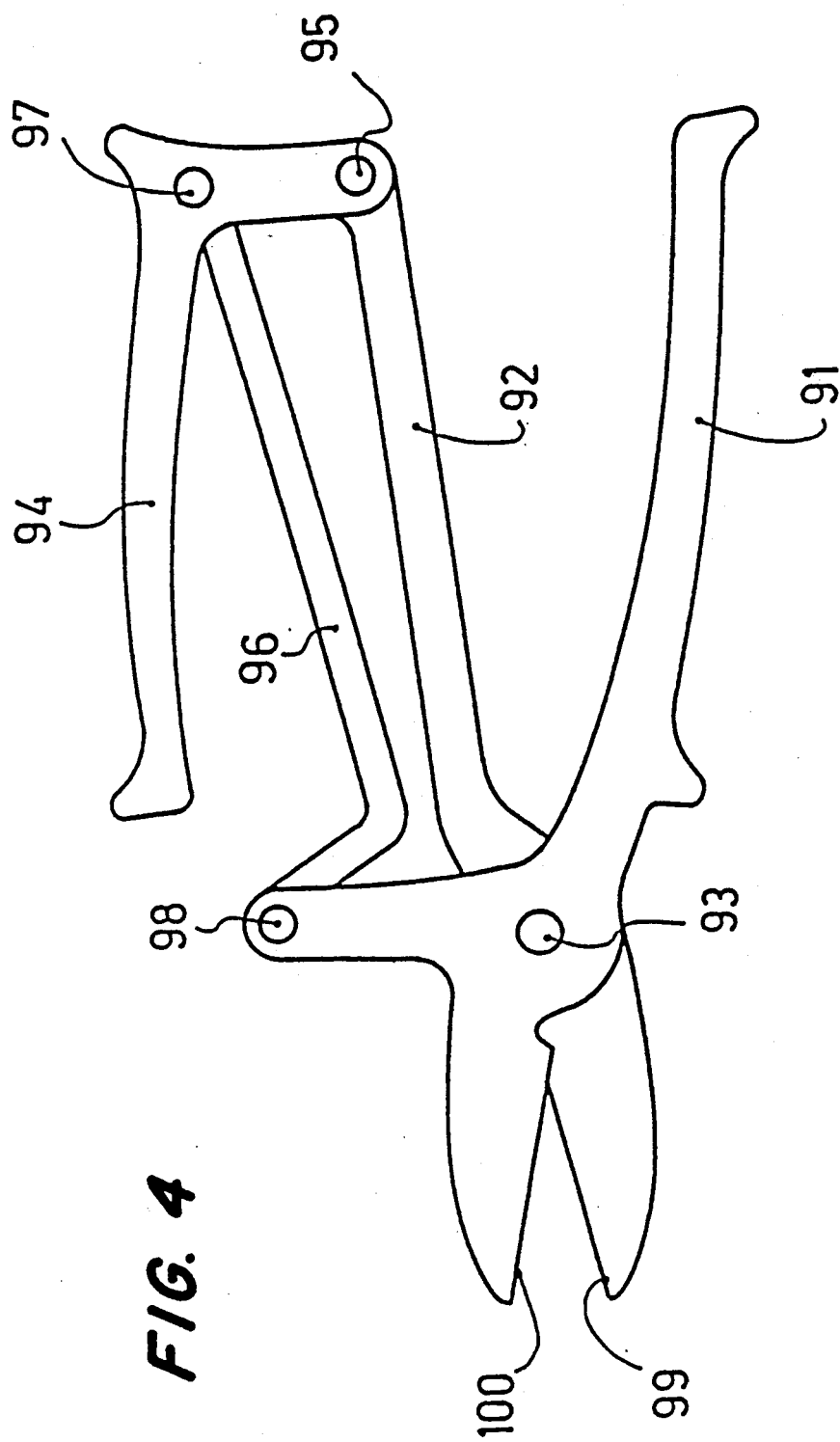
FIG. 4 is a sectional view of a four bar linkage scissors according to the invention.

FIG. 4 represents a four bar linkage scissors according to the invention. Stationary handle 91 is connected to a movable handle 94 through two bars 92,96 which are pivoted at joints 93,95,97 and 98. Hand power is delivered to the blades 99 and 100 through the four-bar linkage movement of the handles 91 and 94 with optimum utilization of the fingers.

I claim:

1. A hand power mechanism to be actuated by the fingers of the human hand for a tool of a type which is designed to be used with the hand oriented so that the index finger is closest to the tool and the little finger is farthest away from the tool, the hand power mechanism comprising
- a stationary handle (101) for fixed attachment to the tool having a surface to be engaged during use by the palm of the hand;
- a drive lever (102) pivotally attached to said stationary handle at a first pivot location (103);
- a movable handle (104) having a surface with locations to be engaged during use by the index, middle, ring and little fingers of the hand, said movable handle being pivotally connected to said drive lever at a second pivot location (105);
- a linkage closure bar (106) pivotally connected to said stationary handle and to said movable handle at third (108) and fourth (107) pivot locations, respectively, spaced from said first and second pivot locations, respectively, so that said linkage closure bar and said drive lever form a four-bar linkage with sections of said stationary handle and said movable handle between said pivot locations,
- said first, second, third and fourth pivot locations being arranged so that when said movable handle is moved by the hand toward said stationary handle, the distance traveled by the index finger of said hand is greater than the distance traveled by the little finger of said hand, thereby providing an optimal force/travel ratio for said fingers.

2. A hand power mechanism according to claim 1 wherein the arrangement of said pivot locations is such that a first line passing through said first and second pivot locations intersects a second line passing through said third and fourth pivot locations on the opposite side of the little finger of the hand from the index finger of the hand.

3. A hand power mechanism according to claim 2 wherein the length of said second line as measured from a position occupied by the little finger to the point of intersection with said first line is about 0.5 to 2.5 times the length of said linkage closure bar.

4. A hand power mechanism according to claim 3 wherein said first, second, third and fourth pivot locations are flexible joints formed by an elastomer.

5. A hand power mechanism according to claim 2 wherein the length of said second line as measured from a position occupied by the little finger to the point of intersection with said first line is about 0.5 to 10 times the distance between the positions to be occupied by the index and little fingers.

6. A hand power mechanism according to claim 5 wherein said first second third and fourth pivot locations are flexible joints formed by an elastomer.

7. A hand power mechanism according to claim 1 wherein said first second third and fourth pivot locations are flexible joints formed by an elastomer.

8. A hand power mechanism according to claim 1 wherein said tool is a caulking gun for dispensing silicone rubber or bone cement.

9. A hand power mechanism according to claim 1 wherein said tool is scissors.

* * * * *